United States Patent [19]

diVincenzo

[11] Patent Number: 5,301,551
[45] Date of Patent: Apr. 12, 1994

[54] WET BULB WICKS FOR CORROSIVE ATMOSPHERES

[76] Inventor: Guido diVincenzo, Rte. 6, Box 240, Asheboro, N.C. 27203

[21] Appl. No.: 844,727

[22] Filed: Mar. 2, 1992

[51] Int. Cl.$^5$ ............................................. G01W 1/00
[52] U.S. Cl. .............................. 73/335.08; 73/29.02; 73/335.06; 428/36.1; 428/190
[58] Field of Search ................ 428/35.8, 36.1, 190, 428/280, 311.1; 73/335, .01, 335.02, 335.03, 335.05, 335.06, 335.08, 29.02

[56] References Cited

U.S. PATENT DOCUMENTS

| | | | |
|---|---|---|---|
| 856,944 | 6/1907 | Cramer | 73/335.02 |
| 956,296 | 4/1940 | Cramer et al. | 73/335.02 |
| 2,128,462 | 8/1938 | Kahn et al. | 73/335.02 |
| 2,284,254 | 5/1942 | Batcheller | 428/280 |
| 2,657,157 | 10/1953 | Francis, Jr. | 428/280 |
| 2,949,394 | 8/1960 | Rodman | 428/280 |
| 3,430,357 | 3/1969 | Perry | 34/16.5 |
| 3,825,007 | 7/1974 | Rand | 428/280 |
| 4,175,436 | 11/1979 | Crawford et al. | 73/338.6 |
| 4,651,780 | 3/1987 | diVincenzo | 137/559 |
| 4,664,959 | 5/1987 | Dagenais et al. | 428/190 |
| 4,809,537 | 3/1989 | Glover et al. | 73/335.02 |
| 5,016,472 | 5/1991 | Amrhein et al. | 73/338 |
| 5,066,527 | 11/1991 | Newell | 428/36.1 |
| 5,098,754 | 3/1992 | Horstmyer | 428/35.2 |

*Primary Examiner*—George F. Lesmes
*Assistant Examiner*—Terrel Morris
*Attorney, Agent, or Firm*—Rhodes, Coats and Bennett

[57] ABSTRACT

Disclosed is a wick for a wet bulb, wherein the bulb is elongated with a free end and a supported end. An absorbent fabric has a portion configured as a folded over sleeve to at least partially closely surround the bulb. The sleeve has two ends, one of which is open and the other of which is closed to permit the open end of the sleeve to be slipped over the free end of the bulb and passed to the supported end until the closed end of the sleeve approaches the free end of the bulb. A plastic film lining inside the sleeve is resistant to corrosive materials to protect the bulb from corrosive materials and has a lower coefficient of friction than the fabric to ease installation over the bulb. A tail contacts a water supply to pick up water and transport it to the sleeve to wet the bulb.

14 Claims, 1 Drawing Sheet

WET BULB WICKS FOR CORROSIVE ATMOSPHERES

BACKGROUND OF THE INVENTION

The present invention relates to improvements in wicks for wet bulb boxes of humidity sensing devices such as hygrometers, RTD sensors and vapor tension sensors, particularly for use in corrosive environments.

In the art of drying lumber, the lumber is dried in a kiln to remove water vapor. The process is monitored using a wet bulb and dry bulb temperature sensors to indicate the conditions of the atmosphere in the kiln. Typically, the humidity and temperature are carefully monitored and controlled to dry the lumber at a selected rate to avoid damaging the lumber. For example, too-rapid drying can cause the lumber to crack or split, but drying too slow is, of course, inefficient.

Wet bulb sensors are well-known. One type is a hygrometer consisting of two temperature sensors for measuring the temperature of an ambient atmosphere. One directly measures the temperature, while the other is kept wet by a wick, so that the cooling effects of evaporating water will cause a temperature difference between the wet and dry sensors. The lower the humidity of the atmosphere, the greater the drying rate and temperature difference. A particularly common device for controlling the rate of lumber drying is a vapor tension controller. In such a controller the wet bulb is provided in the form of a chamber filled with a preselected, pure gas. The chamber is connected via a capillary to controller, so that as the gas in the chamber contrasts or expands with temperature fluctuations, this is communicated to the controller through the capillary. One known controller of this type is made by The Coe Manufacturing Company, Paynesville, Ohio.

However, in drying lumber, the vapors emanating from the lumber include not only water vapor, but also acids. The acids dissolve in the water of the wick of the wet bulb sensor. This problem has been known a long time. Attempts to solve it have taken the form of providing protective coatings on the temperature sensors, but these have not proven to provide sufficiently long-lasting protection. When the corrosion eats through the wet bulb, changes in the gas pressure are no longer accurately communicated to the controller. Repair requires not only replacing the bulb, but also fully evacuating the chamber and some controller components and replacing the pure gas, all of which is quite expensive.

The wicks which are placed on the wet bulb sensors are replaced rather frequently so they can adequately maintain the wet bulb condition. If the wicks become crusty, slimy, torn or otherwise perforated, they lose their effectiveness and transmit a false signal to the wet bulb. The rate of replacement of wicks varies, depending on a number of conditions. For example, in a setting where the water supply is hard, mineral deposits build up quickly on the wick, requiring rapid replacement. Similarly, it is believed that the acids in the atmosphere attack the wick itself, causing its early failure. Because of this and the fact that wicks are inexpensive, they are considered to be short-term, disposable commodities.

Replacement of the worn-out wick in a hot kiln is not a pleasant job. This is particularly so if the temperature sensor has a bit of age, so that corrosion pits and roughens its surface, snagging the wicks.

As a result, those of ordinary skill in the art have a need for an improved wet bulb wick to reduce corrosion of the wet bulb sensor, permit easy installation of a new wick and lengthen the lifetime of wicks.

SUMMARY OF THE INVENTION

The present invention fulfills this need in the art by providing a wick for a wet bulb including an absorbent fabric having a portion configured to at least partially surround the wet bulb. A lining inside this portion is resistant to corrosive materials to protect the bulb from the corrosive materials.

In a preferred embodiment the portion is a sleeve. A preferred fabric is a woven fabric including absorptive cotton fibers bound by polyester yarns.

The lining material can be any suitable material, such as a plastic or metal film. The portion of the wick surrounding the bulb can be formed as a folded over and stitched sleeve. If a thermoplastic film is used as the liner, the sleeve can be conveniently made as a folded over and heat sealed sleeve.

Preferably, the lining has a lower coefficient of friction than the fabric, so the wick can be easily slipped on and off the sensor.

Also preferably, the surrounding portion is configured to closely surround the wet bulb, so that accurate temperatures are reflected.

In a commonly used wet bulb sensor, the wet bulb is elongated with a free end and a supported end. In such a case the wick portion is preferably a sleeve having two ends, one of which is open and the other of which is closed. This permits the open end of the sleeve to be slipped over the free end of the bulb and passes to the supported end until the closed end of the wick approaches the free end of the wet bulb, to protect the free end of the bulb.

The wick also preferably includes a tail for contacting a water supply to pick up water and transport it by capillary action to the surrounding portion to transmit the temperature of evaporation to the wet bulb.

The invention also provides a method of transmitting the temperature of evaporation to a wet bulb temperature sensor. The method includes providing a wick made of an absorbent fabric having a tail and a portion configured to at least partially surround the wet bulb temperature sensor and a lining inside the portion, the lining being impervious to corrosive materials to protect the bulb from corrosive materials. Also provided is a water supply. The method proceeds by positioning the portion of the wick in surrounding relation to the temperature sensor and positioning the tail of the wick in contact with the water supply.

The providing step preferably includes providing a piece of absorbent fabric and applying a piece of lining material adjacent the piece of absorbent fabric. Then, the pieces of absorbent fabric and lining material are folded to form the portion having the lining material interiorly of the absorbent fabric. This is followed by securing the folded pieces of fabric and lining material together along a line of securement so that the portion is on one side of the line and the tail is on the other side of the line. The securing step may include stitching the fabric along the line. Alternatively, the securing step may include heat sealing the lining along the line. The applying step may include fusing the lining material to the absorbent fabric.

BRIEF DESCRIPTION OF THE DRAWINGS

The invention will be better understood after a reading of the Detailed Description of the Preferred Embodiments and a review of the drawings in which.

DETAILED DESCRIPTION OF THE PREFERRED EMBODIMENTS

Figure 1:
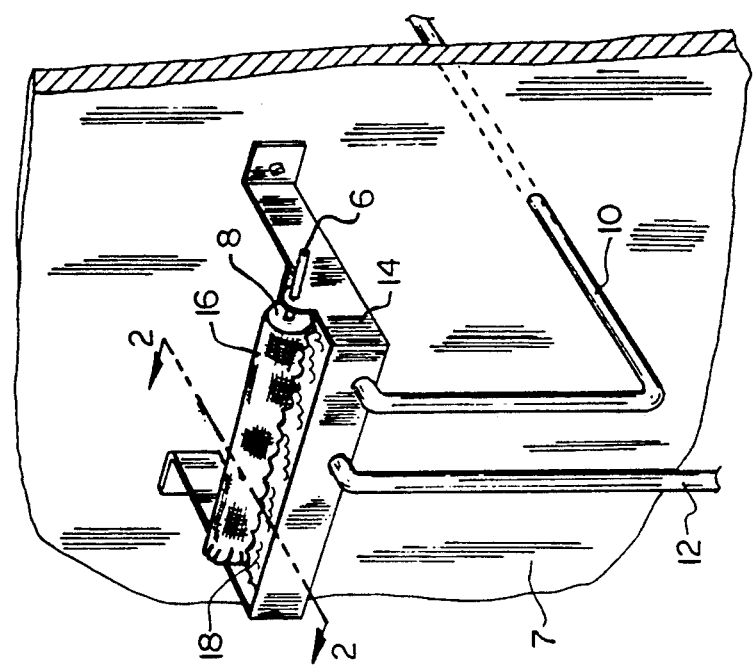
FIG. 1 is a perspective view of a wet bulb box of a vapor tension sensor equipped with the invention.

A wet bulb box is depicted in FIG. 1 as being mounted on a wall 7 of a lumber kiln. As will be appreciated, the invention is applicable to wet bulbs in numerous environments in which the advantages of the invention may be obtained. The wet bulb box 14 is provided with inlet piping 10 and outlet piping 12 to maintain a desired level of water 18 in the box 14, as more fully described in my prior U.S. Pat. No. 4,651,780, the entire disclosure of which is incorporated herein by reference. As shown in FIG. 1, the box 14 supports one end of a temperature sensor 8. Since the sensor 8 is of conventional configuration, it will not be described herein in detail. However, the embodiments contemplated for use with the present invention include thermocouples, RTD sensors and vapor tension sensors, particularly the latter, since some are made of copper and susceptible to corrosion. The temperature sensed by the sensor 8 is communicated along line 6 to a suitable, known control apparatus.

Figure 2:
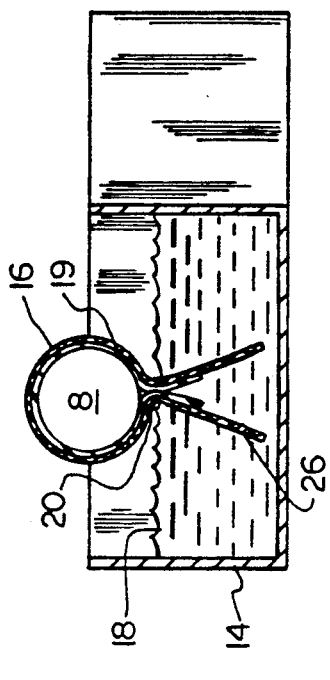
FIG. 2 is a sectional view of the wet bulb box of FIG. 1 taken along lines 2—2 looking in the direction of the arrows.

The temperature sensor 8 is sheathed by a wick 16 in accordance with the present invention. As seen in the sectional view in FIG. 2, the sheath 16 includes an outer layer of fabric 20 and an inner lining 19. The wick fabric includes a tail 26 extending down well into the water 18 in the wet bulb box 14. The fabric 20 of the wick 16 can be of any suitable absorbent configuration. However, a particularly preferred fabric is that used in conventional continuous rental toweling, provided any sizing on the fabric has been washed off. It is thin, but quite absorbent. The fabric structure includes a polyester net base for strength, with cotton fiber interlaced therewith for absorbency.

Interiorly of the fabric 20 is the lining 19. The lining 19 can be any material which permits intimate thermal contact between the fabric 20 and the heat sensor 8, yet prevents the corrosive elements of the kiln atmosphere from reaching the temperature sensor 8. Specifically contemplated are metallic foils and plastic films having melting points above the highest kiln temperature expected. If desired the plastic film can be provided with a pressure sensitive adhesive to facilitate adhering the film to the fabric.

If the lining 19 is made of a thermoplastic material, manufacture of the wick can proceed quite easily, since the plastic can be bonded to the fabric. Then the fabric can be folded and heat-sealed along a securement line to make a sleeve or pocket suitable for at least partially surrounding the sensor.

While various coatings may be suitable for the practice of the invention, any coating on the inside of the wick must not prevent proper wicking action.

Figure 3:
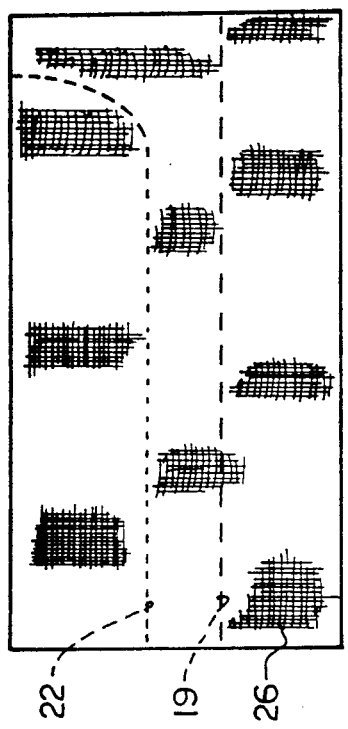
FIG. 3 is a plan view of one embodiment of the invention.
Figure 4:
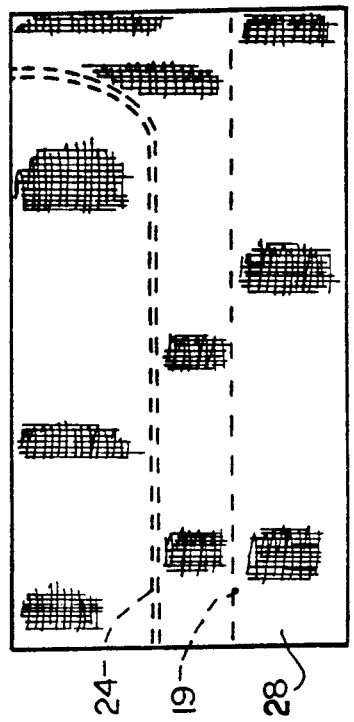
FIG. 4 is a plan view of another embodiment of the invention.

Two embodiments of the wick can be seen in FIGS. 3 and 4. In FIG. 3, the folded over fabric is stitched along a line 22 to form a sleeve which can fit over the free end of the sensor 8. This construction is suitable for any desired lining material. If the lining material is a thermoplastic, the sleeve can be formed by a seal 24, as shown in FIG. 4, to form a pocket or sleeve which can fit over the temperature sensor 8. As can be appreciated, the sleeve has an open end and a closed end.

The lining 19 serves as a barrier to prevent corrosive materials from coming into contact with and therefore corroding the temperature sensor 8. In addition, since the lining material typically has a lower coefficient of friction than the fabric 20, the wick provided with the lining material more readily slips over the temperature sensor 8, even if the temperature sensor 8 has become pitted by earlier corrosion.

And, surprisingly, it has been found that the wicks themselves last longer when provided with the lining material 19 than prior, unlined wicks. It is not known precisely why this is the case, but it may be that the contact of the corrosive material of the atmosphere, as dissolved in the water in the wick, acts on the metal of the temperature sensor 8 to, not only corrode it, but also the wick. With the lining shielding the fabric from the metal of the sensor, anodic and/or cathodic reactions are reduced and therefore less damaging to the wick itself.

Typically, the kiln is operated at a temperature range of from about 95° F. to about 240° F. for lumber drying. The operators of the kilns who, in the past, were asked to replace the wicks much appreciate this invention. The low coefficient of friction of the lining material makes the old wicks slide off easily and new wicks slide on easily, considerably reducing the effort required and shortening the period of time in which they must remain in the heated kiln.

Another advantage of providing the protective lining on the wick is that, as the wick is replaced, the protection of the sensor provided by the lining is renewed. Thus, any corrosive attack of the lining will not ultimately lead to corrosion of the temperature sensor. This should be contrasted with the prior attempts to protect sensors by coating them. Once that coating is corroded, the sensor is open to attack.

The wick with the lining closely contacts the temperature sensor so that the difference in temperature of the bulb caused by the evaporation from the wick is accurately transmitted to the temperature sensor.

As will be appreciated, various modifications to the invention as specifically disclosed herein can be carried out by those of ordinary skill in the art, and such modifications are deemed to be within the scope of this invention.

What is claimed is:

1. A wet bulb arrangement comprising a wet bulb, an absorbent fabric having a portion configured to surround said wet bulb and a lining inside the portion, said lining being attached to said absorbent fabric and resistant to corrosive materials to protect said bulb from corrosive materials while permitting intimate thermal contact between the absorbent fabric and the bulb.

2. An arrangement as claimed in claim 1 wherein said portion is a sleeve.

3. An arrangement as claimed in claim 1 wherein said lining is a plastic film.

4. An arrangement as claimed in claim 1 wherein said fabric is a woven fabric including absorptive cotton fibers and polyester.

5. A wick as claimed in claim 1 wherein said portion is formed as a folded over and stitched sleeve.

6. A wick as claimed in claim 1 wherein said portion is formed as a folded over and heat sealed sleeve.

7. An arrangement as claimed in claim 1 wherein said lining has a lower coefficient of friction than said fabric.

8. An arrangement as claimed in claim 1 for a wet a bulb that is elongated with a free end and a supported end, wherein said portion is a sleeve having two ends, one of which is open and the other of which is closed to permit said open end of said wick to be slipped over the free end of the bulb and passed to the supported end until said closed end approaches the free end, to protect the free end of the bulb.

9. A wet bulb arrangement as claimed in claim 1 wherein the absorbent fabric includes a tail for contacting a water supply to pick up water and transport water to the configured portion for transmitting the temperature of evaporation to the bulb.

10. A method of transmitting the temperature of evaporation to a wet bulb temperature sensor comprising:
providing a wick made of an absorbent fabric having a tail and a portion configured to be in intimate contact with the bulb temperature sensor and a lining inside the portion, the lining being attached to the absorbent fabric and resistant to corrosive materials encountered to protect the bulb from corrosive materials and allowing intimate thermal contact between the absorbent fabric and the bulb,
providing a water supply,
positioning the portion of the wick in surrounding relation to the temperature sensor and
positioning the tail of the wick in contact with the water supply.

11. A method as claimed in claim 10 wherein said providing step comprises
providing a piece of absorbent fabric,
applying a piece of lining material adjacent the piece of absorbent fabric,
folding the pieces of absorbent fabric and lining material to form the portion having the lining material interiorly of the absorbent fabric, and
securing the folded pieces of fabric and lining material together along a line of securement so that the portion is on one side of the line and the tail is on the other side of the line.

12. A method as claimed in claim 11 wherein said securing step includes stitching the fabric along the line.

13. A method as claimed in claim 11 wherein said securing step includes heat sealing the lining along the line.

14. A method as claimed in claim 13 further wherein said applying step includes fusing the lining material to the absorbent fabric.

* * * * *